United States Patent
Folestad et al.

(10) Patent No.: US 8,024,154 B1
(45) Date of Patent: Sep. 20, 2011

(54) METHODS AND DEVICES FOR EVALUATING MATERIAL IN A PHARMACEUTICAL PROCESS

(75) Inventors: Staffan Folestad, Mölndal (SE); Lubomir Gradinarsky, Mölndal (SE)

(73) Assignee: AstraZeneca AB, Södertälje (SE)

( * ) Notice: Subject to any disclaimer, the term of this patent is extended or adjusted under 35 U.S.C. 154(b) by 978 days.

(21) Appl. No.: 11/793,394

(22) PCT Filed: Dec. 20, 2005

(86) PCT No.: PCT/SE2005/001974
§ 371 (c)(1),
(2), (4) Date: Jun. 19, 2007

(87) PCT Pub. No.: WO2006/068598
PCT Pub. Date: Jun. 29, 2006

(30) Foreign Application Priority Data

Dec. 22, 2004 (SE) ...................................... 0403151

(51) Int. Cl.
*G21C 17/01* (2006.01)
(52) U.S. Cl. ...................................................... 702/182
(58) Field of Classification Search .................... 702/22, 702/32, 38, 57, 134, 182, 183; 367/137
See application file for complete search history.

(56) References Cited

U.S. PATENT DOCUMENTS

| | | | |
|---|---|---|---|
| 4,943,713 A | 7/1990 | Yoshida | |
| 4,955,004 A * | 9/1990 | Viscovich | 367/137 |
| 5,480,050 A | 1/1996 | Morrow et al. | |
| 5,970,434 A | 10/1999 | Brophy et al. | |
| 2003/0024315 A1* | 2/2003 | Merkel et al. | 73/596 |
| 2003/0033870 A1* | 2/2003 | Shah et al. | 73/299 |

FOREIGN PATENT DOCUMENTS

| | | |
|---|---|---|
| DE | 102 59 830 | 7/2004 |
| GB | 2 141 997 | 1/1985 |
| JP | 8-136512 | 5/1996 |

* cited by examiner

*Primary Examiner* — Mohamed Charioui
(74) *Attorney, Agent, or Firm* — Finnegan, Henderson, Farabow, Garrett & Dunner, LLP

(57) ABSTRACT

A device and a method in processing, such as pharmaceutical processing, is provided. At least one signal is transmitted in a processing structure which is adapted to receive materials. The propagated signal is received and a parameter value thereof is compared with a reference value. The presence of materials or any other geometrical change in the processing structure is evaluated based on the comparison. The signal may be in the form of an electromagnetic wave, e.g. a microwave. Also, a use of a processing vessel, or a pipe connected to such a vessel, is provided.

28 Claims, 3 Drawing Sheets

METHODS AND DEVICES FOR EVALUATING MATERIAL IN A PHARMACEUTICAL PROCESS

TECHNICAL FIELD

The present invention relates to a method in processing, such as pharmaceutical processing. The invention also relates to a processing device, such as a pharmaceutical processing device, and to a use of a processing vessel, such as a pharmaceutical processing vessel, or of a pipe connected to such a vessel.

BACKGROUND OF THE INVENTION

The use of production lines with long pipe or piping structures is common in many industries, such as the pharmaceutical industry, the chemical industry, the food industry, etc. These pipe structures are generally used to convey materials to or from a vessel, or to convey materials between two vessels. For instance, in the production of pharmaceutical dosage forms, such as tablets or capsules, the ingredients are processed or conveyed in different processing structures. One processing structure may be a granulation vessel, another processing structure may be a drying vessel, yet another processing structure may be a pipe for leading materials or substances from the granulation vessel to the drying vessel. Also a system of several processing vessels and/or pipes can be regarded as a processing structure.

In the production of pharmaceuticals it is desirable to reduce the risk of mixing materials from different batches or reduce the risk of leaving high-risk substances, such as high-potency drugs or chemically or microbiologically reactive materials, inside the processing structure. It is also desirable to detect any geometrical changes on the interior of the processing structure, such as damaged or disconnected portions of the processing structure, so that the personnel may take appropriate actions at an early stage. Apart from changes on the actual processing structure or its components, a geometrical change may also be a change in the amount of material inside the processing structure.

In the present situation, the manufacturing personnel have to gain access to the interior of the processing structure in order to perform manual cleanness tests or a damage check. In some cases such tests may be difficult to execute, e.g. depending on the dimensions of the processing structure, the location of the processing structure, or even the location to be cleaned or inspected inside the processing structure. Also, by not knowing whether or not the processing structure is free from material remains, or if other geometrical changes have occurred, the personnel will tend to check the processing structure more often than necessary, resulting in unnecessary time loss and additional production costs.

Thus, it would be desirable to detect any material remains from processes from different batches, or to detect other changes in the internal geometry of processing structures, in an easy and reliable manner. It would also be desirable to reduce possible time loss and production costs.

SUMMARY OF THE INVENTION

An object of the present invention is to alleviate the drawbacks of the prevailing manual tests. This and other objects, which will become apparent in the following, are accomplished by the methods, the devices and the uses defined in the independent claims.

The present invention is based on the insight that use may be made of an existing structure for determining the presence of material remains inside the structure or other changes in the internal geometry of the structure. By allowing an existing processing structure to act as part of a detection arrangement which conveys information which can be related to the geometry or environment inside the structure, the personnel does not have to open the structure to gain access to the inside in order to obtain the information. Thus, by using the existing processing structure as an information carrier the detection of any material remains or other geometrical changes may be performed substantially non-invasively and/or non-destructively.

It should be noted that, in this application, the term "processing structure" includes not only vessels, dryers, mixers or the like in which a material is treated, but also includes any pipe or other tubular structure or container in a production line through which the material is transported or contained without being subjected to any particular treatment. Furthermore the term "processing structure" is not limited to mean only a single pipe or a single vessel, but can also be construed as a combination of pipes or vessels, or any other combination of these items. In other words, the term "processing structure" is herein used to include either a single item, such as a vessel or a pipe, or any combination of such items in a system configuration.

The present invention is applicable in various types of industries, some non-exhaustive examples being the pharmaceutical industry, the chemical industry, the food industry, the metallurgical industry and the agricultural industry, however other alternative types of industries are also possible. Thus, it should be understood that the present invention is not limited to any particular field of processing or any particular processing device, however, for explanatory purposes and ease of understanding, the following description will mainly be related to the pharmaceutical industry.

The terms "material", "pharmaceutical material" or "pharmaceutical substance" are herein to be interpreted as including at least any one of the items from the group consisting of powders, powders in combination with water or other liquid, solids, solids in combination with water or other liquid, slurries, liquids and suspensions. It may also be a combination of said items. It should also be understood that pharmaceutical materials and is substances are not limited to meaning only one or more active components, but it may also mean one or more non-active components, generally referred to as excipients, or a combination of active and non-active components.

The information related to the geometry inside the structure is suitably conveyed by means of a signal introduced into the processing structure, the signal being any detectable physical quantity or impulse by which information can be transmitted. Depending on the interior geometry of the structure, the presence or absence of objects, and the like, the signal may be affected in different ways. By analysing how signals are affected it is possible to determine whether or not the interior conditions of the processing structure has changed from one time to another.

Thus, according to one aspect of the invention a method in processing, such as pharmaceutical processing is provided. The method comprises: providing materials, such as pharmaceutical materials, in a processing structure, such as a vessel or a pipe, or any combination of one or more vessels and/or pipes; removing materials from said processing structure; and thereafter transmitting at least one signal to be propagated in said processing structure, and, suitably, also guided by said processing structure; receiving the thus propagated signal; and comparing at least one parameter value of the received signal with a reference value to evaluate if there is any remaining material in the processing structure or any geometrical change in the processing structure.

Similarly, according to a second aspect of the invention a processing device, such as a pharmaceutical processing device is provided. The device comprises a processing structure, such as a vessel or a pipe, or any combination of one or more vessels and/or pipes, for processing or transporting materials (e.g. pharmaceutical materials) in or through said processing structure; at least one transmitter for transmitting at least one signal to be propagated in said processing structure; at least one receiver for receiving the thus propagated signal; and an analysing unit, such as a computer or microprocessor, operatively connected to the receiver for determining a parameter related to the received signal. Suitably, the analysing unit may also be operatively connected to the transmitter.

The information carrying signal may have different parameters. For instance, if the signal comprises a wave, it may be described by parameters such as phase, amplitude, power and frequency. The wave may be an electromagnetic wave or an acoustic wave which is propagated through the processing structure, wherein the phase, amplitude, power and/or the frequency of the wave will be differently affected depending on the presence or absence of pharmaceutical material or other geometrical changes inside the processing structure. Alternatively, the signal may comprise a combination of an electromagnetic wave and an acoustic wave. It should be noted that an acoustic wave (also referred to as pressure wave) does not necessarily mean that it constitutes an audible sound, but rather that it is a wave in which the propagated disturbance is a variation of pressure in a medium. Alternatively, the signal may be an electric current which may be affected by a changed resistance, capacitance, etc. due to changes in the interior of the processing structure. In such case, the processing structure may suitably be insulated.

As mentioned previously, an electromagnetic wave may be used for conveying information related to the interior condition of the processing structure. Therefore, according to at least one embodiment of the invention said processing structure is used as a waveguide. Consequently, the embodiment comprises transmitting at least one electromagnetic wave to be propagated in said processing structure, receiving the thus propagated electromagnetic wave, and comparing at least one parameter value of the received electromagnetic wave with said reference value.

According to at least one embodiment, the processing structure is made of metal or any other material which is suitable for guiding an electromagnetic wave.

As previously, explained the parameter may e.g. be the amplitude, the power, the phase or the frequency of the wave. For instance, information regarding the interior condition of the processing structure may be obtained by comparing the detected value of the amplitude of the received signal with a reference or set amplitude value. Suitably, if the difference between the detected value and the reference value exceeds a predetermined difference it is considered indicative of a changed condition inside the processing structure. Said predetermined difference may either be zero or a non-zero value. In this context a changed condition means that the condition inside the processing structure at the time the signal was received is different from a condition at an earlier occasion. The changed condition may thus be a change in the amount of pharmaceutical material present in the processing structure, or a geometrical change in the wall due to damage. The changed condition may suitably be detected based on a changed dielectric constant or at least a change in either of its real part or imaginary part. For instance, if the processing structure is empty the dielectric constant for air is known, and if some pharmaceutical or other foreign material remains are present inside the processing structure the dielectric constant may be different, affecting the amplitude and/or the phase of the propagating signal. If it is established that there is a changed condition, the personnel may take appropriate measures, e.g. cleaning or repairing the processing structure, before it is brought into use again. If it is established that there is no changed condition, the personnel does not need to spend time on accessing the interior of the processing structure.

Any interruption of the process or other general control of the process, e.g. if a changed condition has been detected which calls for some kind of action being taken, may be performed manually or automatically. Therefore, in general terms at least one embodiment of the invention comprises controlling the process on basis, at least partly, of the detected parameter or parameter value. The act of controlling the process may e.g. comprise at least the act of stopping the process. However, if the obtained parameter or parameter value does not require any action to be taken, the act of controlling the process may e.g. comprise at least the act of continuing the process or provide new material to be treated, etc. This control is suitably performed automatically, for instance by an analysing and control unit mentioned below. The controlling may follow a flow chart having a feedback-loop or some other general type of controlling scheme. The controlled process may be a batch process, wherein one batch of material at a time is processed, or a continuous process wherein material is processed continuously. Suitably, in connection with a continuous process, the acts of transmitting a signal, receiving the signal and evaluating the information are performed continuously for monitoring the progress of the process. However, these acts may also be performed continuously within one batch process. Note that the term "continuously", may include measurements at several discrete moments, however at substantially steady intervals or a certain repetition frequency rather than at random. An integrated parameter value of the signal over time may be used as a reference value in a continuous measurement. Apart from the above mentioned acts of controlling, an act of controlling the process may include performing repair work.

The reference parameter value is suitably determined before pharmaceutical material is introduced into the processing structure, i.e. in a clean condition or state of the processing structure. Transmission and reception of one or more signals is performed in such a clean state in a corresponding manner to the subsequent transmission and reception when establishing any changed condition of the processing structure. Thus, by transmitting into the "clean" processing structure a signal having one or more specified parameter values and receiving the thus propagated signal and determining the value of the parameter or parameters, an initial response is obtained and a calibration is achieved. When pharmaceutical materials are later introduced and removed, a change from the calibrated state may be detected, suitably by transmitting a signal having the same parameter values as signal transmitted at the time of calibration. If the received signal differs from the initial response it is indicative of a change inside the processing structure, such as remaining pharmaceutical particles or alternatively some other geometrical change such as a damaged wall. An alternative for setting the reference value, is to make theoretical mathematical calculations. Another alternative is to perform simulations, e.g. computer simulations, in order to determine a reference value for a "clean" processing structure. Yet another alternative, as will be described below, is the case wherein it is desired to calibrate for a non-zero amount, such as a predetermined filling level. Thus, in a general sense, the calibration may be expressed as determining the reference value by transmitting at least one signal to be propagated in said processing structure when a known amount, such as a zero or non-zero amount, of pharmaceutical material is present in processing structure, receiving the thus propagated signal, and determining the value of at least one parameter related to the received signal.

The information conveyed by the existing processing structure may be contained in an applied microwave radiation. According to at least one embodiment of the invention said signal comprises at least one electromagnetic wave, wherein said electromagnetic wave has a frequency in the range of 100 MHz to 3 THz, e.g. in the form of a microwave frequency in the range of 300 MHz to 300 GHz. In a pharmaceutical production line, the dimensions of the tubular structures and vessels are generally in the order of microwave wavelengths, is the microwave region being known to use components comparable in size to their wavelengths. Microwave radiation has a good penetrating capacity compared to other types of radiation, e.g. NIR. Even though microwaves penetrate pharmaceutical powder, they are affected and become distorted, e.g. changed amplitude or phase, thereby making detection possible. Microwaves can be controlled to fill out the entire cavity into which they are introduced, i.e. the microwaves are able to reach corners and other small spaces. It should be noted that the use of microwaves functions for processing structures having circular profile or cross-section, as well as for processing structures having rectangular profile or cross-section. If the entire processing structure does not have a single continuous cross-section, the processing structure may for calculations be considered as consisting of several sections of different profiles or cross-sections.

For a processing structure in the form of a pipe having a circular profile with diameter d the wavelength $\lambda$ of the microwave signal used may suitably be selected in the region of approximately $1.3d \leq \lambda \leq 1.7d$ in order to obtain a single mode electromagnetic propagation. The single mode propagation provides predictability and repeatability of the measurements in the system. The system could utilise higher order propagation modes, generated when using $\lambda < 1.3d$, even though this may decrease the sensitivity to system changes and reduce the performance predictability, due to the mutual interference of the coexisting propagation modes. In the case of rectangular pipe profiles having dimensions a·b the wavelength suitably used will lie in the interval $a \leq \lambda \leq 2a$, where we assume that a>b. The hereby obtainable single mode propagation will again provide a good sensitivity and measurement repeatability. In the case of a=b (wherein $a \leq \lambda \leq 2a$) or $\lambda < a$ higher order propagation modes will appear having similar consequences as in the circular case with higher order propagation modes. If the processing structure is in the form of a production vessel, the selection of which frequency or frequencies to be used could be performed using simulations, since the more complex electromagnetic environment may require a more specific and situation adjusted selection of frequency or frequencies. In summary the applicability of the suggested approach is not limited by which frequency or frequencies (wavelength (s)) will be selected, but could be improved in terms of performance and predictability if such adjustments/considerations taking into account the is particular system set-up are used. It should be noted that even though the application mainly describes using a signal of at least one wavelength, the invention and its aspects and embodiments are not limited to using only a single wavelength or frequency. Thus, the invention also encompasses transmitting signals to be propagated in the processing structure in the form of a plurality of electromagnetic waves of a plurality of frequencies. In other words several information carrier signals may be used within the scope of the invention.

According to at least one embodiment of the invention a transmission mode or a reflection mode of operation is used, or even a combination of said modes of operation. In the transmission mode the signal, suitably in the form of an electromagnetic wave, travels from a first location of the processing structure where it was transmitted to a second location of the processing structure. For instance, the two locations may be at two opposite sides of the processing structure. However, other alternatives are also possible. During its propagation from the first location to the second location, the signal may become affected by the geometry or the presence of any material inside the processing structure. This may result in a distortion of the signal which may be detected at the second location. In the reflectance mode, the propagated signal is reflected when reaching an inner surface of the processing structure before being received. The reflected signal is suitably received at the same location as the one from which it was transmitted. This may be realised by first using an antenna for transmitting the signal and then using the same antenna for receiving the reflected signal. Alternatively, or as a complement, another antenna at another location may receive the reflected signal.

According to at least one embodiment of the invention said at least one transmitted signal, suitably comprising at least one electromagnetic wave, is received at two or more locations, advantageously by means of two or more receivers, such as receiving antennas, at their respective location. The signal or signals may either be transmitted from a single transmitter, such as a transmitting antenna, or alternatively by at least two transmitters. If several transmitters are used, each one of them may have an associated receiver. By arranging the transmitter/receiver pairs at different designated locations and studying their respective responses, it may be possible to detect in which area inside the processing structure pharmaceutical material remains are present.

Another advantage of using several transmitters and receivers is that it becomes easier to detect smaller objects, e.g. small particles, in particular if the measurements are to be performed over a long distance. Therefore, depending on the area or areas in which it is desired to make measurements, and the desired detectable object size, it may be decided how many transmitters and receivers should be used. Instead of covering irrelevant areas where it is known that material does not generally remain, the sensors (transmitters/receivers) may be placed at areas which are more likely to present detectable material remains. If desired, the sensors may be identifiable or differentiated by different methods, e.g. a unique frequency being associated with each transmitter or each transmitter using a unique signal encoding, or any other suitable multiple access method. It is also conceivable to use only one transmitter which emits signals in a decided frequency band, e.g. comprising the microwave frequency region, and several receivers arranged to detect a respective frequency sub-band.

Alternatively, or as a complement to having transmitters and receivers at different locations, an array of receivers and/or transmitters may be provided on a common module. Such transmitter/receiver arrays may be provided in one-dimensional format, wherein the transmitters and/or receivers are arranged along a line, or in a two-dimensional format, wherein the transmitters and/or receivers are arranged in a rectangular matrix. Other formats are also possible. This type of array provided as a module may either be regarded as a large antenna made up of several sub-antennas, or each transmitter and/or receiver on the module may be regarded as a plurality of stand-alone antennas. Said plurality of antennas may therefore be regarded as located at essentially the same location relative to the processing structure or possibly as located at "different" locations but only separated by a relatively short distance. It should also be understood that several arrays may be used simultaneously for measurement on a processing structure.

According to at least one embodiment of the invention one or more reflectors may be located in the propagation path of the transmitted signal in order to at least partially block the propagation of the transmitted signal and at least partially reflect the transmitted signal. The use of reflectors may enable a larger amount of different measurements to be made. For instance, by positioning a reflector in the signal propagation path inside the processing structure the signal will be partially reflected and suitably received at the same side of the reflector, thereby obtaining one possible measurement mode, and by removing the reflector allowing the signal to be propagated along its path and received at a location further away another measurement mode is made possible. Also, if the reflector is at least partially transparent to the signal, the reflected part of the signal may be received on one side of the reflector while the transmitted part of the signal may be received on the other side of the reflector. It is also conceivable to use a reflector for which it is possible to vary how much of the signal is to be reflected, for instance by varying the effective blocking area of the reflector.

The person skilled in the art will understand that by varying the number of reflectors used or the location of the one or more reflectors further information regarding e.g. material remains may be obtained. In particular, by using reflectors it may facilitate the finding of the approximate location of such material remains.

The reflectors may be used for at least partially closing or sealing off at least one portion of the processing structure. Thus, according to at least one embodiment of the invention the reflectors may be in the form of one or more closure or sealing elements, such as valves, sliding gates or the like. By closing off the processing structure a limited space may be obtained for measurements. This may for example be used for determining the approximate location of material remains or damages in the processing structure. Thus, by sealing off different portions and performing measurements therein, it can be determined in which sub-space or sub-spaces of the processing structure any change has occurred when compared to a reference state of the sub-space or sub-spaces. However, as previously mentioned, the reflector does not necessarily have to completely block the propagation of the signals, the same principle with sub-spaces being applicable also with partly transparent reflectors.

The reflectors in the form of closure or sealing elements may be already existing valves in the processing structure. The valves may be open when material is transported therethrough and may be closed before performing a measurement for checking whether there is any material remains left. Alternatively, it is contemplated that additional reflectors may be applied to existing processing structures, e.g. if it is desirable to obtain more or smaller sub-spaces for facilitating the locating of the intrusion in the form of e.g. material remains or other interior geometrical changes.

Furthermore, the use of reflectors allows a single unit or a small number of transmitters and receivers to be used for the measurements in a processing structure. For instance, if a unit which is located at one end of a processing structure is used as both transmitter and receiver, reflectors may be activated in a certain order for performing reflectance mode measurements in different sub-spaces. Thus, a signal may be transmitted towards a first reflector which reflects the signal at least partially, and the received reflected signal being compared with a reference. Afterwards, that reflector is opened or inactivated and another reflector further away or nearer to the transmitter/receiver unit is activated before performing a new measurement, etc. In this way it is possible to find an approximate location of e.g. material remains by checking which measurement indicated possible presence of material remains and which measurement did not indicate presence.

Also, a first processing structure in the form of a pipe, could be used to couple electromagnetic energy into a second processing structure, such as a bigger processing vessel. An advantage of this is that probes already present on the first processing structure may be used for obtaining information about the state inside the second processing structure. Thus, the first processing structure may be regarded as a transmitter and/or receiver antenna per se.

It should be noted that even though the description has been focused on measurements performed on one processing structure in a production line, the inventive methods may be used at several processing structures. Thus, there may be a pair of or an array of transmitters and receivers arranged e.g. at a granulation vessel, another pair or array at a drying vessel, and yet another pair or array at a pipe connecting the two vessels. Alternatively, there may be a pair of one transmitter in a first processing structure and one receiver in a second processing structure. The receivers, and suitably also the transmitters, at each processing structure may be operatively connected to a single common analysing unit, such as a computer or microprocessor. Alternatively, each processing structure may have its own designated analysing unit.

Thus, from the above it should be clear that the present invention contemplates the use of a transmitter and receiver placed at different locations or at the same location (e.g. as one unit). The invention also contemplates the use of a single or multiple transmitters and receivers, with a possibility to set them in an array along the production system.

For implementing at least one embodiment of the invention, the one or more transmitters and receivers may be arranged exteriorly of the processing structure. In such case, the processing structure may suitably be provided with a window or some other wall portion which is at least partly transparent to the transmitted signal, thereby enabling the transmitted signal to be entered into the processing structure, and also enabling the propagated signal to exit the processing structure for detection by the one or more receivers. Alternatively, a portion of the wall may be openable for enabling one or more transmitters and/or receivers to be introduced as probes into the processing structure. The probes may suitably be introduced automatically e.g. after pharmaceutical material has been removed from the processing structure.

It has been described above to use a processing structure as a waveguide for implementing the invention. The processing structure may e.g. be an already existing part of a processing system. However, it is also conceivable to do it the other way around, i.e. to incorporate a waveguide into the processing system, even though the waveguide in some cases is obtainable from other suppliers than the other parts of the system. Once incorporated, the waveguide may be used as a processing structure for receiving, containing, transporting and/or treating pharmaceutical materials. This implementation is encompassed by a third aspect of the invention.

Thus, according to the third aspect of the invention a method in processing, such as pharmaceutical processing is provided. The method comprises providing a waveguide configured and dimensioned for directing the propagation of electromagnetic waves, such as microwaves; providing materials in said waveguide; processing or transporting the materials in or through said waveguide; removing materials from said waveguide; transmitting at least one signal, in the form of an electromagnetic wave, to be propagated in said waveguide; receiving the thus propagated electromagnetic wave; and using at least one parameter related to the received electromagnetic wave to evaluate if there is any remaining material in the waveguide or any geometrical change in the waveguide.

Corresponding to the method according to the third aspect of the invention, a processing device, such as a pharmaceutical processing device is provided in accordance with a fourth aspect of the invention. Said device comprises a waveguide configured and dimensioned for directing the propagation of electromagnetic waves, such as microwaves, wherein the waveguide, comprises an inlet for introducing materials into the waveguide and an outlet, preferably separate from the inlet, for removing materials from the waveguide. Even though the inlet will generally be separate from the outlet, it is also conceivable that the same port is used as both inlet and outlet. Said device further comprises at least one transmitter for transmitting at least one signal, in the form of an electromagnetic wave, to be propagated in said waveguide and at least one receiver for receiving the thus propagated electromagnetic wave, and said device also comprises an analysing unit, such as a computer or microprocessor, operatively connected to the receiver for determining a parameter related to the received electromagnetic wave. The analysing unit may either provide visual or audible information to the personnel, so that a decision may be made whether any action should be taken in the processing structure, e.g. for repairing the processing structure or for cleaning the processing structure from material, or on the contrary for adding more material as will be described below. Some actions may be taken automatically without necessarily informing the personnel, e.g. if after a batch has been removed and no material remains are detected a valve controlled by the analysing unit may be opened for allowing a new batch to enter the processing structure.

It should be understood that the third and fourth aspects of the invention encompass any embodiments or any features described in connection with the first and second aspects of the invention, as long as those embodiments or features are compatible with the use of the waveguide of the third and fourth aspects.

It should be understood that a waveguide controls the propagation of an electromagnetic wave so that the wave is forced to follow a path defined by the physical structure of the guide. A waveguide of a given dimension will not propagate electromagnetic waves lower than a certain frequency (the cutoff frequency). At least some of the aspects and embodiments of the present invention utilises the processing structure as a guiding means for guiding the electromagnetic wave along the processing structure.

The above described aspects of the invention and the different embodiments thereof have mainly been described in relation to detecting material remains, such as pharmaceutical material remains, after removal of material from the processing structure, or detecting other interior geometrical changes such as a damaged, loose or disconnected portion of the processing structure. However, an internal geometrical change may also be a change in the amount of material from one time to another. For instance, when it comes to detecting material remains, the amount is zero before any material is introduced into the processing structure. After the material is attempted to be removed, any remains will be a non-zero amount. In another situation it may be desirable to fill the processing structure with material up to a predetermined level, i.e. a predetermined amount. After some filling, the measurements may indicate that the level has not yet been reached, i.e. the measured amount is not equal to the predetermined amount. Therefore, further filling, suitably automatically, may be performed by means of the analysing unit which may be operatively connected to a material supply source for controlling the adding of more material. A new measurement is then made to detect if there has been an interior geometrical change, i.e. if the desired predetermined amount has been reached. Thus, the detection of this type of internal geometrical change, which not only relates to structural changes, but also to a change in contents or amount, is also encompassed by the previously mentioned aspects of the invention. Furthermore, all the above types of detection are encompassed by a fifth aspect of the invention.

In accordance with the fifth aspect of the invention a method in processing, such as pharmaceutical processing is provided. The method comprises providing a processing structure, such as a vessel, a pipe or a combination thereof such as a combination of one or more vessels and/or pipes, which is adapted to receive materials (e.g. pharmaceutical materials). The processing structure is used as a waveguide by transmitting at least one signal in the form of at least one electromagnetic wave to be propagated along and guided by the processing structure. The thus propagated electromagnetic wave is received, wherein at least one parameter value of the received electromagnetic wave is compared with a reference value related to a reference state of the interior of the processing structure. Based on the comparison of said values, it is evaluated whether the present state of the interior of the processing structure is different from said reference state.

It should be noted that the term "present state" is meant to be interpreted as the state at the point of time when the propagated signal was received and measured. It should therefore not be limited to the state of the processing structure at the exact time when the evaluation or interpretation of the signal is performed which could be at a later stage.

As described above it may be desirable to detect a change in the amount of material inside the processing structure. Thus, according to at least one embodiment of the invention the reference state and the present state may be related to material content in the processing structure, wherein the processing structure contains a first amount of materials in the reference state and a second amount of materials in the present state. Therefore, said at least one embodiment comprises evaluating whether said second amount is different from said first amount.

As mentioned above the first amount may be a zero (empty processing structure) or non-zero amount, and likewise the second amount may be a zero or non-zero amount (in the non-zero cases it is assumed that any material property changes are negligible). If the reference state is a state in which a predetermined non-zero amount of material is present in the processing structure, the personnel may measure the present state e.g. to ensure that the actual amount stays below the predetermined amount, or to ensure that it reaches the predetermined amount, or to ensure that it exceeds the predetermined amount. This could be achieved by using several additional predetermined reference states apart from a desired reference state. The additional reference states will indicate the presence of higher or lower levels of material compared to the desired reference state. Thus, according to at least one embodiment of the invention, the method further comprises changing, such as by adding or removing, the amount of material inside the processing structure, based on the evaluation of whether the second amount is different from the first amount. This may suitably be accomplished automatically, by means of a feedback or control system.

It should be noted that apart from what has been described above, the fifth aspect of the invention encompasses any embodiments or any features described in connection with the previously described aspects of the invention, as long as those embodiments or features are compatible with the use of the processing structure as a waveguide.

Furthermore, the insight of using an existing processing structure as a waveguide is set forth in accordance with a sixth aspect of the invention, which provides a use of a processing vessel (e.g. a pharmaceutical processing vessel), or a pipe connected to such a vessel, as a waveguide for detecting the presence of material (e.g. pharmaceutical material). Similarly in accordance with a seventh aspect of the invention there is provided a use of a processing vessel (e.g. a pharmaceutical processing vessel), or a pipe connected to such a vessel, as a waveguide for detecting a change over time in the amount of material (e.g. pharmaceutical material) therein. Thus, by using the processing structure as waveguide it is possible to make a measurement at a first point of time, suitably in accordance with the above described methods, and another measurement at a second point in time, and comparing the responses in order to determine whether the amount has changed between the measurements.

An additional way of using a processing structure (e.g. pipe or vessel) as a microwave guiding device is by employing a resonance mode of operation. A microwave resonator can be defined as section of a transmission line bound by impedance discontinuities (impedance transition borders). In the case of pipe structure, the discontinuities could be formed at both ends of the pipe. They could be open circuit—transition from a waveguide structure to air (e.g. open valves) or a short-circuit—transition in a waveguide structure closed by metal plate (e.g. closed valves). In the case of vessel structure the whole structure itself can be regarded as a hollow resonator. The field inside the resonator is excited by coupling of a transmitter/receiver system in ways similar to the above or below discussed cases. Resonance will occur if the excited field is in-phase with the one reflected at the impedance transition borders. The conditions for that are varying depending on the discontinuities types (air, metal etc.), on the type of resonance structure used (waveguide, coaxial etc.), its dimensions and on the frequency used, but generally speaking the phase difference between the input and the reflected energy should be $n \times 2\pi$ for the effective wavelength of the propagated energy (n is an integer number). The parameters associated with resonances are the resonant frequency and/or the Q-factor (the ratio of the energy stored in the resonator to the energy dissipated during 1 cycle). In accordance with the applications of the invention, the frequency used for a resonance to occur is adjusted. Measurements of the change of the resonant frequency and/or the Q-factor with respect to the initially established reference state may be used to indicate presence of material remains or changes of other character. For example, in the cases of material remains determination, reaching the predetermined reference value of the resonance frequency and/or the Q-factor will indicate that the predetermined state (empty structure) has been reached. Similarly, when a presence of certain amount of material is the reference state, reaching the predetermined resonance frequency/Q-factor will indicate its achievement. An advantage of using a resonance mode of operation is that it may be performed by using a single transmitter/receiving unit. Another advantage is the high sensitivity to changes in the environment in the measured structure. However, if desired the use of several units is a possible alternative.

Apart from enabling detection of e.g. material remains after a process has been performed in a processing structure, the invention may also be implemented for continuous monitoring of a process. Thus, according to an eighth aspect of the present invention there is provided a method of monitoring a process of transporting an amount of material through a processing structure (e.g. a pharmaceutical processing structure) such as a vessel, a pipe or a combination thereof such as a combination of one or more pipes and/or vessels. This method of monitoring transportation of an amount of material comprises using the processing structure as a waveguide by repeatedly or continuously transmitting signals in the form of electromagnetic waves to be propagated along and guided by the processing structure, receiving the thus propagated electromagnetic waves, and comparing at least one parameter value of the received electromagnetic waves with a reference value that is indicative of a reference state of the interior of the processing structure before said amount of material has been introduced into the processing structure. When said amount of material is introduced into the processing structure said parameter value will become different from said reference value and when said amount of material has been transported through and out of the processing structure said parameter value will return to substantially correspond to said reference value.

Thus, by noticing how the response changes during the monitoring it is possible to see when material has been, or is being, added to the processing structure as well as when material has been, or is being, removed from the processing structure. Even though it may be practical to use an empty processing structure as a reference level, a partly filled processing structure could also be conceivable. The latter case may be used e.g. for monitoring whether a substantially even amount of material is flowing through the processing structure, wherein a change in the response indicates if there has been an increase or a decrease in the material flow.

It should be noted that apart from what has been described above, the eighth aspect of the invention encompasses any embodiments or any features described in connection with the previously described aspects of the invention, as long as those embodiments or features are compatible with the use of the processing structure as a waveguide.

In the following a number of non-limiting embodiments of the present invention will be given with reference to the accompanying drawings.

DETAILED DESCRIPTION OF THE DRAWINGS

Figure 1A:
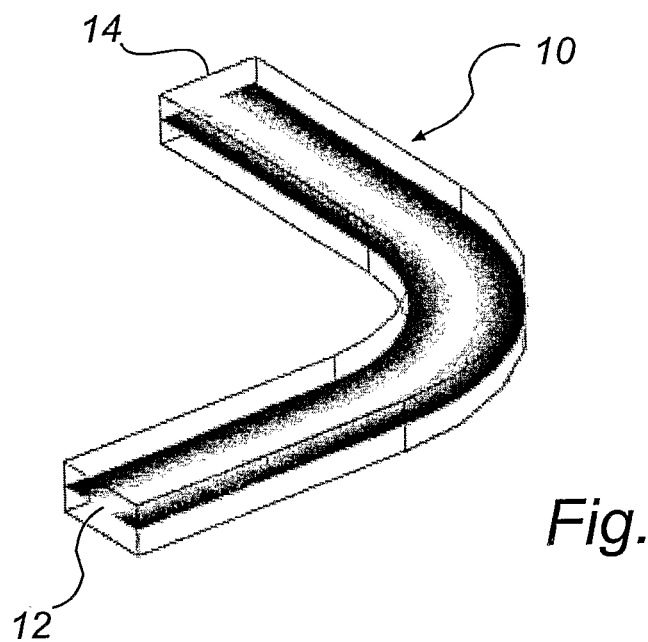
FIG. 1a and FIG. 1b illustrate schematically an underlying principle of at least one embodiment of the invention, wherein it is illustrated how different dielectric constants affect an electromagnetic power flow through a processing structure or waveguide.
Figure 1B:
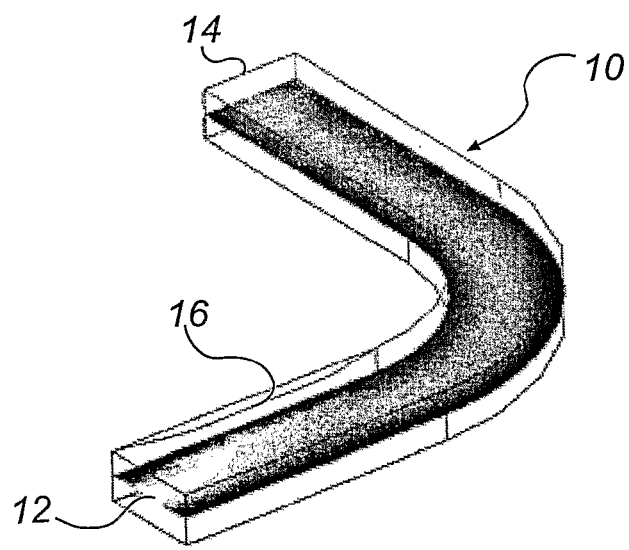

FIG. 1a and FIG. 1b illustrate schematically an underlying principle of at least one embodiment of the invention, wherein it is illustrated how different dielectric constants affect an electromagnetic power flow through a processing structure (pipe) or waveguide 10. The waveguide 10 has a rectangular profile in these figures, however, the corresponding principle applies also to other profiles.

The waveguide 10 illustrated in FIG. 1*a* is empty, i.e. the only dielectric medium inside the waveguide 10 is air. Electromagnetic energy, e.g. microwave energy, is transmitted into the waveguide 10 through an input end 12 thereof. We assume ideal coupling of the electromagnetic energy at the input end 12 and a single mode of propagation. The distribution of the electromagnetic power flow through the waveguide 10 is indicated by the different shades of a grey scale representative of the power intensity, wherein white is high intensity and black is low or no intensity. As can be seen from FIG. 1*a*, the propagated electromagnetic wave has not lost any power when it reaches the other end 14 of the waveguide, seen from the figure by the same power intensity. The power flow distribution is almost constant throughout the waveguide 10.

In FIG. 1*b* the illustrated waveguide 10 contains a small amount of pharmaceutical material 16, such as e.g. powder, that has a dielectric constant which is different from that of air. The pharmaceutical material 16 is located near the input end of the waveguide 10 as indicated by the contour on the side of the waveguide 10. Due to the dielectric constant of the pharmaceutical material 16 an electromagnetic wave transmitted through the input end will be affected differently than if only air would have been present inside the waveguide 10. As illustrated in FIG. 1*b* there is a substantial power loss as the electromagnetic wave propagates through the pharmaceutical material 16 (illustrated by the bright shade quickly transforming into a darker shade along the pharmaceutical material 16), and there is a clear difference between the electromagnetic power flow in the waveguides of FIG. 1*a* and FIG. 1*b*. This detectable difference at the output 14 or anywhere along the waveguide may be used for detecting the presence of material remains.

Also, it should be understood that this principle of detectable difference may also be used e.g. for establishing the amount of material present in a processing structure, such as a vessel. The attenuation of the propagating electromagnetic energy may be regarded as substantially proportional to the amount of material that it propagates through. Therefore, let us assume that a processing structure, such as a vessel, e.g. a granulation vessel, is to be filled with a certain amount of material, wherein said amount is expected to attenuate 50% of the power of the electromagnetic energy that is propagated through the material (here, for simplicity, field distribution effects are neglected). If, after an initial supply of material into the processing structure, it is detected that the power of the electromagnetic energy that has propagated through the material is higher than 50% of the transmitted power, the interpretation would be that said certain amount of material has not yet been reached. Thus, it should be clear from above that even though FIG. 1*a* and FIG. 1*b* show a waveguide 10 or a processing structure in the form of a pipe, the principle is also usable in other processing structures, such as vessels or portions thereof.

Also, an acoustic wave or any other signal which is differently affected by air and other materials may be used for detecting the presence of material remains or the amount of material.

Furthermore, any damage or disconnected portion of a processing structure may also cause a different attenuation to the electromagnetic energy power compared with an intact processing structure. In this connection it should be understood that the invention may also be used for detecting whether two processing structures have become at least partly disconnected.

Figure 2:
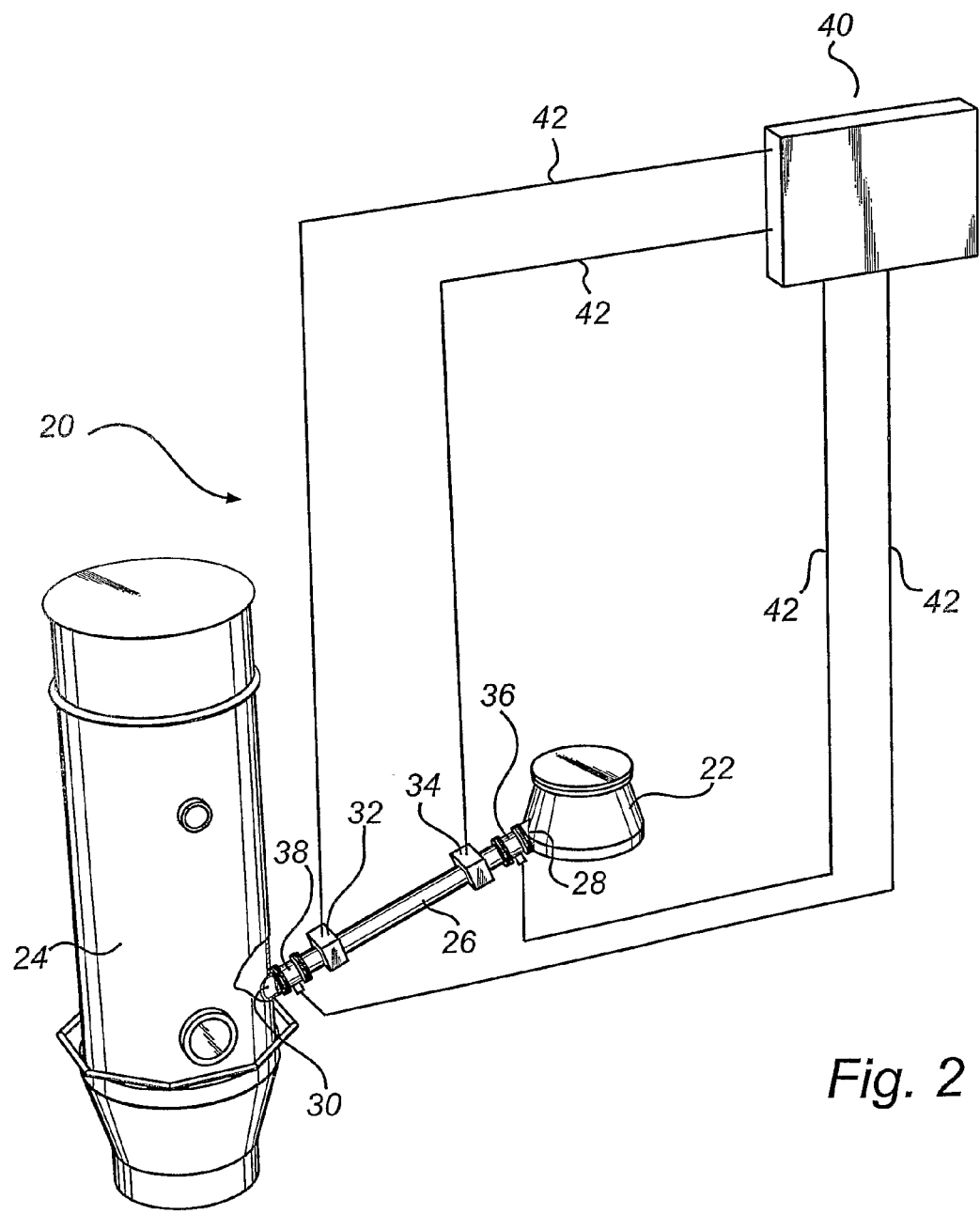
FIG. 2 illustrates schematically parts of a pharmaceutical processing system in which at least one embodiment of the present invention has been implemented.

FIG. 2 illustrates schematically parts of a pharmaceutical processing system 20 in which at least one embodiment of the present invention has been implemented. One of the shown parts of the pharmaceutical processing system 20 is a granulation vessel 22 in which an active ingredient is mixed with a filler and a binding substance, such as water. Another part is a drying vessel 24 in which the mixed pharmaceutical materials are dried to obtain a desired low water content. A connecting part in the form of a pipe 26 allows the mixed material in the granulation vessel 22 to be transferred to the drying vessel 24. The granulation vessel 22 has one or more inlets (not shown) for receiving the material to be mixed, and has also an outlet 28 from which the mixed material may enter into the pipe 26. Similarly, the drying vessel 24 has an inlet 30 connected to the pipe 26 for receiving the mixed materials, and one or more outlets (not shown) for outputting the sufficiently dried materials for further processing. The outlet 28 of the granulation vessel 22 is arranged on a vertically higher level than the inlet 30 of the drying vessel 24, thereby allowing the gravitation to act on the mixed materials for transporting it through the inclined pipe 26, however other arrangements for promoting transport through the pipe may also be provided.

There are two sensors or probes 32, 34 provided on the pipe 26, in this embodiment comprising antennas for transmitting and/or receiving electromagnetic radiation, suitably in the form of microwaves. However, in other embodiments they could be acoustic probes. The antennas 32, 34 may be insertable through the wall of the pipe 26 or be arranged to transmit and receive electromagnetic radiation outside the pipe 26 through a window which is at least partly transparent to electromagnetic radiation.

A first valve 36 is provided at the outlet 28 of the granulation vessel 22 and a second valve 38 is provided at the inlet 30 of the drying vessel 24. One function of the valves 36, 38 is to control the material flow. For instance, before the materials in the granulation vessel 22 have been mixed to a desired degree at least the first valve 36 is closed so as to prevent material from leaving the granulation vessel 22. Another function of the valves 36, 38 is to delimit a space for facilitating electromagnetic radiation measurements and to act as a reflector which reflects the propagating electromagnetic waves. The use of the valves as reflectors allows a single unit to function as both transmitter and receiver. Also if the system is suitably adjusted and there is a disturbance (e.g. material remains), the signal will be more attenuated since it will pass the disturbance twice or more and there will therefore be a greater detectable difference to a reference signal. Furthermore, a resonance mode may be used, as has been described previously herein.

Also, in accordance with at least one embodiment of the invention an analysing unit 40 is connected at least to one of the antennas 32, 34 which receives the propagated electromagnetic wave. A parameter value, such as amplitude or phase is compared with a reference value of that parameter in order to determine the state of the pipe 26, e.g. whether there are any material remains after material has been allowed to flow into the drying vessel 24 from the pipe 26. However, as illustrated in FIG. 2, the analysing unit 40 may also be operatively connected to the other components, i.e. the other antenna and the valves 36, 38, and will in the following therefore be generally referred to as an analysing and control unit 40. The analysing and control unit 40 is herein illustrated with wires 42 connected to the different components. However, the control unit 40 may also be operatively connected to said components by other means, e.g. radio control or coaxial lines wherein the microwaves are conducted all the way to the analysing and control unit 40.

In at least one mode of operation, the sufficiently mixed materials are passed from the granulation vessel 22 through the pipe 26 and into the drying vessel 24. Thereafter, a command signal may be sent from the analysing and control unit 40 to close the valves 36, 38, or the valves 36, 38 may be manually closed. Next, the analysing and control unit 40 activates one of the antennas 32, 34 to transmit electromagnetic radiation in the form of one or more electromagnetic waves which will propagate inside the pipe 26 and will be received by the other antenna. The analysing and control unit 40 will analyse the contents of the received electromagnetic wave, e.g. by comparing the amplitude of the wave with the expected amplitude response for an empty pipe 26. If there is a difference which is indicative of there being remaining pharmaceutical material in the pipe 26 or that the pipe 26 has been damaged or disconnected, the analysing and control unit 40 will alert the personnel so that appropriate action may be taken (e.g. cleaning or repairing). However, if the evaluation performed by the analysing and control unit 40 indicates that the pipe is sufficiently clean, the analysing and control unit 40 may open the valves 36, 38 once new materials have been satisfactorily mixed in the granulation vessel 22.

It should be noted that the valves 36, 38 in FIG. 2 do not necessarily have to be closed when transmitting the electromagnetic radiation. The measurements may still provide satisfactorily distinguishable information. Thus, during the propagation of the electromagnetic wave inside the pipe both valves 36, 38 could be open, or one of the valves could be open while the other one is closed.

It should also be noted that either one of the two antennas 32, 34 may act as a receiving and/or transmitting antenna. Thus, it need not necessarily be the case that one transmits and the other one receives. It could very well be the case that only one antenna is used, e.g. antenna 32, and that said antenna both transmits and receives the electromagnetic wave. Alternatively, both antennas 32, 34 could transmit simultaneously and also receive the electromagnetic waves. Another alternative is that one of the antennas, e.g. antenna 32, acts as a transmitting and receiving antenna while the other antenna 34 acts only as a transmitting antenna or only as a receiving antenna. The locations of the antennas 32, 34 may be chosen from general electromagnetic considerations for constructive interference. For taking advantage of the reflecting function of the valves or similar reflectors, it has e.g. been found suitable to locate the antennas at a distance of $n\lambda/4$ from the valves, wherein n is an odd positive number (n=1, 3, 5, . . . ). The frequency or frequencies used may be chosen depending on the geometry of the pipe 26.

It should also be noted that even though FIG. 2 illustrates only two antennas 32, 34, another number of antennas may be provided. For instance, there may be provided a single antenna working in reflection mode (the valves suitably being closed), or there may be provided more than two antennas, e.g. in several groups or arrays.

Figure 3:
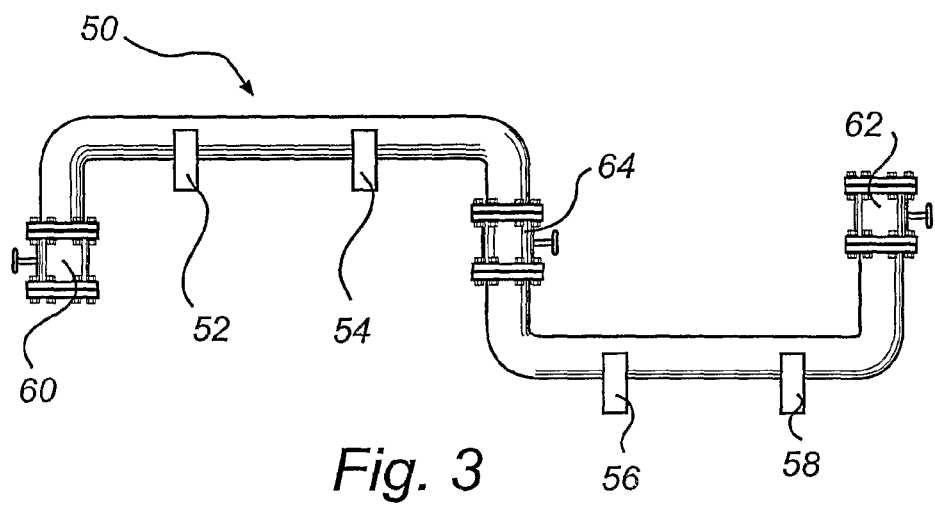
FIG. 3 illustrates schematically a processing structure in which at least another embodiment of the present invention has been implemented.

FIG. 3 illustrates schematically a processing structure in which at least another embodiment of the present invention has been implemented. The processing structure is in the form of a long pipe 50 or a system of several pipes connected together. If several pipes are connected together, they may include a pipe having a larger diameter connected to a pipe having a smaller diameter, or the pipes may have equal diameters. The pipe 50 may be some type of connecting pipe similar to the one shown in FIG. 2 or some other type of supply or discharge pipe in a pharmaceutical processing system. Even though no analysing or control unit is illustrated in FIG. 3, such a unit may suitably be provided.

Due to the length of the winding pipe 50 several antennas may be provided. In the illustrated embodiment there are provided four antennas 52, 54, 56, 58. The antennas may act as transmitters and/or receivers in any combination. There is also provided a first valve 60 at one end of the pipe 50, a second valve 62 at the other end of the pipe 50 and a third valve 64 halfway along the pipe 50. The valves 60, 62, 64, which may be opened and closed, act as reflectors in their closed position, wherein an incident electromagnetic wave will be at least partly reflected by the closed valve (some transmission may be allowed). The measurements may be performed with all the valves 60, 62, 64 closed, or all open, or with one or two open.

By combining measurements at the different antennas 52, 54, 56, 58, it is possible to approximate the location of where remaining pharmaceutical material or a damage may be present. By closing the third valve 64, it would be possible to determine on which side of the valve 64 remaining material may be present. It would also be possible to use only one of the antennas, e.g. antenna 52, as a transmitter and receiver and while the illustrated valves 60, 62, 64 or more valves are closed sequentially so that measurements in several subspaces of the pipe 50 may be performed in order to find the approximate location of an intrusion in the form of remaining material or other geometrical change in the pipe 50 such as a damaged wall portion. The person skilled in the art will realize that there are several other ways and variations of using the antennas 52, 54, 56, 58 and valves 60, 62, 64 for finding the approximate location of any remaining material. Also, it would be conceivable to arrange a vessel instead of a pipe portion between e.g. valves 62 and 64 with all previously described combination of measurement possibilities. Thus, e.g. antenna 52 could be used as a transmitter and an antenna (corresponding to 56 or 58) on a vessel arranged after valve 64 could be used as a receiver.

Figure 4:
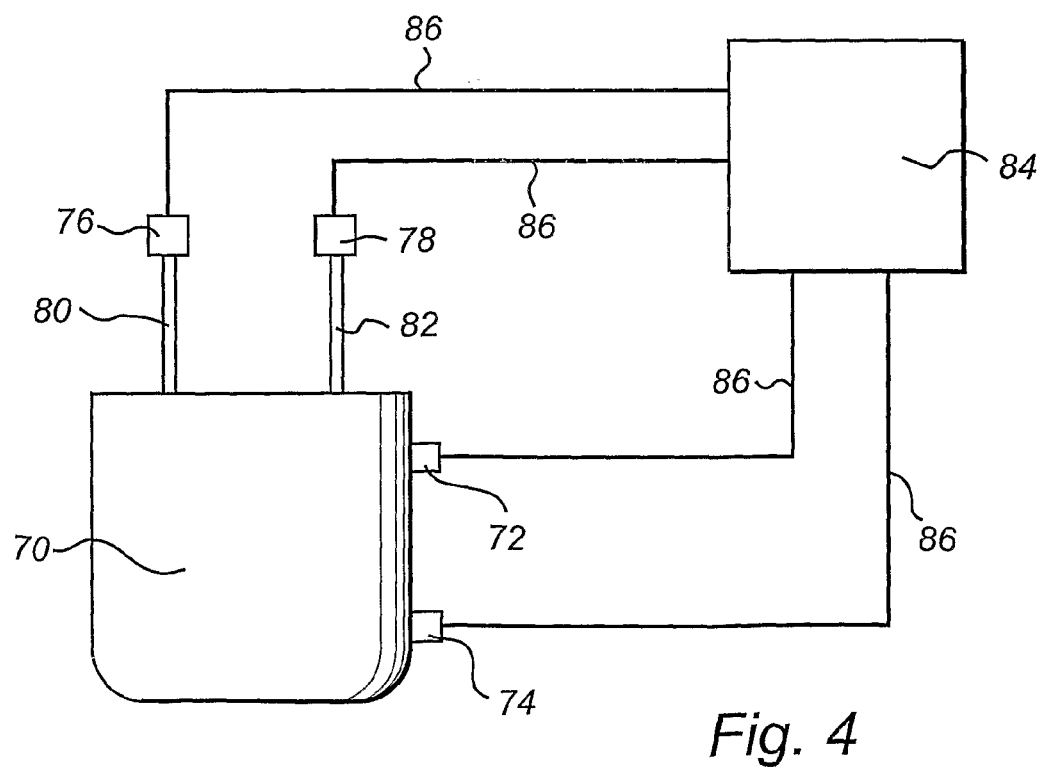
FIG. 4 illustrates another processing structure in which at least yet another embodiment of the present invention has been implemented.

FIG. 4 illustrates another processing structure 70 in which at least yet another embodiment of the present invention has been implemented. The processing structure 70 defines a contained space. The below described conducted measurements could be applicable to any type of pharmaceutical production vessel, but in this figure it is intended to illustrate measurements in a granulation vessel 70. On the wall of the vessel 70 there are provided two probes comprising antennas 72, 74, however, there may be another number. One of the antennas, e.g. antenna 72, may be a transmitter while the other antenna 74 may be a receiver, or alternatively one or both of the antennas 72, 74 may act both as transmitter and receiver. The choice of frequency and antenna location is determined by employing general electromagnetic theory.

FIG. 4 also illustrates two supply sources 76, 78 from which different pharmaceutical materials may be feed into the production vessel through respective supply lines 80, 82. An analysing and control unit 84 is operatively connected, e.g. by means of wires 86 or radio control, to both the supply sources 76, 78 and the antennas 72, 74. Based on the information contained in the received electromagnetic wave(s), the analysing and control unit 84 may control the supply sources to feed more material into the vessel 70 until the received electromagnetic wave has appropriate parameter value(s) when compared to one or more corresponding reference values. The analysing and control unit 84 may also be used in an operating mode for detecting whether there is any material left in the vessel 70 after material has been discharged therefrom.

It should be noted that the set-ups in FIG. 2, FIG. 3 and FIG. 4 may be used in any combination with each other or with other set-ups. For instance, in the illustrated set-up of the system parts in FIG. 2 the granulation vessel 22 could also be provided with probes 72, 74 as illustrated in FIG. 4, wherein those probes could be operatively connected to a specific analysing and control unit 84 or to the same unit 40 as the probes 32, 34 in FIG. 2. Furthermore, the drying vessel 24 in FIG. 2 may also be fitted with probes so as to enable the detection of any remaining pharmaceutical material after discharge, the detection of whether a filling level has been achieved or whether any damage has occurred on the drying vessel 24, etc. Thus, probes may be present on both a production vessel and a on pipe to such a vessel. Furthermore, the invention may be implemented on other types of pharmaceutical processing devices than those illustrated in the figures. It should also be understood that the invention may be implemented in different types of pharmaceutical processes. For instance, the invention may be implemented in both a batch process and/or a continuous process.

The invention claimed is:

1. A method for evaluating the presence of a pharmaceutical material in a pharmaceutical process, comprising:
   providing the pharmaceutical material to a processing structure, the processing structure including at least one of a vessel or a pipe,
   removing at least part of the pharmaceutical material from said processing structure,
   transmitting at least one signal to be propagated in said processing structure,
   receiving the thus propagated signal,
   comparing at least one parameter value of the received signal with a reference value, and
   evaluating, based on the comparison of said values, if there is any remaining pharmaceutical material in the processing structure.

2. The method as claimed in claim 1, comprising
   using said processing structure as a waveguide, wherein transmitting a signal comprises transmitting at least one electromagnetic wave to be propagated in said processing structure, and wherein receiving the signal comprises receiving the thus propagated electromagnetic wave,
   wherein comparing at least on parameter value of the received signal comprises comparing at least one parameter value related to the received electromagnetic wave with said reference value.

3. The method as claimed in claim 2, wherein said electromagnetic wave has a frequency in the range of about 300 MHz to about 300 GHz.

4. The method as claimed in claim 2, wherein said received electromagnetic wave is a reflected wave received at substantially the same location from where it was transmitted, wherein the transmission and reception are preferably performed by means of a single antenna.

5. The method as claimed in claim 2, wherein a first antenna is used for transmitting the electromagnetic wave and a second antenna is used for receiving the propagated electromagnetic wave.

6. The method as claimed in claim 2, comprising receiving said at least one electromagnetic wave at two or more locations by at least two antennas.

7. The method as claimed in claim 2, comprising transmitting electromagnetic waves from two or more locations by at least two antennas.

8. The method as claimed in claim 2, comprising at least one of transmitting and receiving at least one electromagnetic wave from at least one of an array of transmitters and an array of receivers provided on a common module.

9. The method as claimed in claim 1, wherein the signal is transmitted in a direction substantially parallel to a direction of flow of the pharmaceutical material.

10. The method as claimed in claim 9, wherein the direction of signal transmission is with the direction of flow of the pharmaceutical material.

11. The method as claimed in claim 9, wherein the direction of signal transmission is against the direction of flow of the pharmaceutical material.

12. The method as claimed in claim 1, wherein transmitting a signal comprises transmitting at least one acoustic wave to be propagated in said processing structure, and wherein receiving the signal comprises receiving the thus propagated acoustic wave,
   wherein comparing at least one parameter value of the received signal comprises comparing at least one parameter value related to the received acoustic wave with said reference value.

13. The method as claimed in claim 1, comprising determining the reference value by, when a known amount of material is present in processing structure, transmitting at least one signal to be propagated in said processing structure, receiving the propagated signal, and determining the value of at least one parameter related to the received signal.

14. The method as claimed in claim 1, wherein said at least one parameter is selected from the group consisting of an amplitude, a phase, a power, and a frequency of the received signal.

15. The method as claimed in claim 1, comprising using at least one reflector in the propagation path of the transmitted signal in order to at least partially block the propagation of the transmitted signal and at least partially reflect the transmitted signal.

16. The method as claimed in claim 1, comprising adjusting the frequency of the signal to be transmitted so that a resonance will occur in the processing structure, wherein measurements are performed in a resonance mode of operation.

17. The method as claimed in claim 1, wherein said pharmaceutical material is a powder.

18. The method as claimed in claim 1, wherein the signal is transmitted into an input end of the processing structure.

19. A method for evaluating a processing structure used in a pharmaceutical process, the processing structure comprising a lumen adapted to receive materials, the method comprising:
   providing the processing structure,
   using the processing structure as a waveguide by transmitting at least one signal in the form of at least one electromagnetic wave to be propagated along a longitudinal axis of the lumen and guided by the processing structure,
   receiving the propagated electromagnetic wave;
   comparing at least one parameter value of the received electromagnetic wave with a reference value related to a reference state of the interior of the processing structure; and
   evaluating, based on the comparison of said values, if the present state of the interior of the processing structure is different from said reference state.

20. The method as claimed in claim 19, wherein said states are related to material content in the processing structure, wherein the processing structure contains a first amount of material in the reference state and a second amount of material in the present state, wherein the method comprises evaluating, based on the comparison of said values, whether said second amount is different from said first amount.

21. The method as claimed in claim 20, wherein said first amount is substantially zero and the method comprises evaluating whether there is any material in the processing structure.

22. The method as claimed in claim 20, wherein said first amount is a non-zero amount of material and the method comprises determining whether a certain filling level has been reached.

23. The method as claimed in claim 20, further comprising changing the amount of material inside the processing structure based on the evaluation of whether the second amount is different from the first amount.

24. The method as claimed in claim 19, further comprising controlling the pharmaceutical process based on said at least one parameter, wherein the action of controlling comprises at least stopping the pharmaceutical process and continuing the pharmaceutical process.

25. The method as claimed in claim 19, wherein at least the transmitting, receiving, and evaluating are performed continuously for monitoring the progress of the pharmaceutical process.

26. The method as claimed in claim 19, wherein said states are related to the internal geometry of the processing structure, the processing structure has a first internal geometry in the reference state at a first point of time and a second internal geometry in the present state at a second point of time, and the method comprises evaluating, based on the comparison of said values, if a geometrical change on the interior of the processing structure has occurred between said first and second points of time.

27. A method for evaluating a solid material in a pharmaceutical process, comprising:

providing a waveguide configured for directing the propagation of electromagnetic waves, providing the solid material in said waveguide, transporting at least part of the solid material in said waveguide, removing at least part of the solid material from said waveguide, transmitting at least one signal, in the form of an electromagnetic wave, to be propagated in said waveguide, receiving the propagated electromagnetic wave, and using at least one parameter related to the received electromagnetic wave to evaluate an amount of the solid material remaining in the waveguide.

28. A method of monitoring a process of transporting an amount of material through a pharmaceutical processing structure, the pharmaceutical processing structure comprising at least one of a vessel or a pipe, comprising:

using the processing structure as a waveguide by transmitting signals in the form of a plurality of electromagnetic waves to be propagated along and guided by the processing structure, receiving the propagated plurality of electromagnetic waves;

comparing at least one parameter value of the received plurality of electromagnetic waves with a reference value that is indicative of a reference state of the interior of the processing structure before said amount of material has been introduced into the processing structure; wherein when said amount of material is introduced into the processing structure, said parameter value will become different from said reference value, and when said amount of material has been transported through the processing structure, said parameter value will about equal said reference value.

* * * * *